United States Patent

Goddard et al.

[11] Patent Number: 6,071,683
[45] Date of Patent: Jun. 6, 2000

[54] IMAGE DYE-FORMING COUPLERS AND PHOTOGRAPHIC ELEMENTS CONTAINING THEM

[75] Inventors: John D. Goddard, Pinner; Danuta Gibson; Llewellyn J. Leyshon, both of Watford, all of United Kingdom; Brian Thomas, Pittsford, N.Y.

[73] Assignee: Eastman Kodak Company, Rochester, N.Y.

[21] Appl. No.: 09/131,851

[22] Filed: Aug. 7, 1998

[30] Foreign Application Priority Data

Aug. 17, 1997 [GB] United Kingdom .................. 9717166

[51] Int. Cl.$^7$ ........................................................ G03C 1/08
[52] U.S. Cl. ............................................. 430/557; 430/551
[58] Field of Search ........................... 430/543, 556–557, 430/551

[56] References Cited

U.S. PATENT DOCUMENTS

| | | | |
|---|---|---|---|
| 5,215,877 | 6/1993 | Tomotake et al. | 430/557 |
| 5,219,716 | 6/1993 | Takada et al. | 430/557 |
| 5,270,156 | 12/1993 | Hirabayashi et al. | 430/557 |
| 5,324,625 | 6/1994 | Hirabayashi et al. | 430/557 |
| 5,336,592 | 8/1994 | Chino et al. | 430/557 |
| 5,340,703 | 8/1994 | Masumi et al. | 430/557 |
| 5,376,508 | 12/1994 | Yamada et al. | 430/557 |
| 5,380,639 | 1/1995 | Ishige et al. | 430/557 |
| 5,382,506 | 1/1995 | Tosaka et al. | 430/557 |

*Primary Examiner*—Geraldine Letscher
*Attorney, Agent, or Firm*—Arthur E. Kluegel

[57] ABSTRACT

The present invention relates to a silver halide photographic element comprising a dye-forming coupler of formula (I)

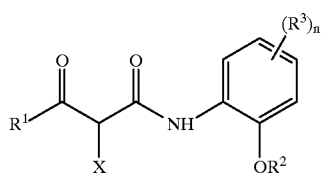

(I)

wherein $R^1$ is selected from an alkyl group, an aryl group, a 5–10 membered heterocyclic group containing one or more O, N or S atoms, each of which groups is unsubstituted or substituted, or a substituted amino group;

$R^2$ is an unsubstituted alkyl group having a secondary or tertiary carbon atom attached to the oxygen atom;

X is hydrogen or a coupling-off group; and $R^3$ is a substituent and n is 0 to 4; or wherein $R^2$, as defined above, and an $R^3$ substituent may together with the O atom form a 5–10 membered heterocyclic group which may contain one or more further heteroatoms selected from O, N and S, said group being unsubstituted or substituted; and wherein at least one of $R^1$, $R^2$ and $R^3$ separately or in combination constitutes a ballast group, the couplers providing enhanced light stability together with acceptable dye hue in images produced from photographic materials containing them.

23 Claims, No Drawings

IMAGE DYE-FORMING COUPLERS AND PHOTOGRAPHIC ELEMENTS CONTAINING THEM

FIELD OF THE INVENTION

This invention relates to image dye-forming couplers, specifically yellow dye-forming couplers, for use in conventional and redox-amplified silver halide color photographic materials and to color photographic materials containing such couplers.

BACKGROUND OF THE INVENTION

In any polychromatic chromogenic photographic material it is desirable that the dyes so formed should have certain properties. For instance the dyes should be bright in color with very little secondary absorption so that good color reproducibility is obtained. For yellow dyes in particular, color purity is enhanced by ensuring that the absorption maximum of the dye is well separated from that of the magenta dye, and hence yellow dyes that absorb at shorter wavelengths are advantageous. It is also paramount that the formed photographic images should be resistant towards fading by heat, humidity and light. When the dye images are formed in silver halide photographic materials from the combination of oxidized developer and an incorporated coupler, certain restrictions are placed on the properties of the coupler. For instance, the coupler should produce a dye which has the aforementioned desirable properties. Also, the coupler itself must show high efficiency in the dye-forming reaction, must be easily dispersible, must itself be resistant towards the deleterious effects of light, heat and humidity and must have a low propensity to form fog.

In the field of acetanilide-based couplers it is known that incorporating an alkoxy substituent in the 2-position of the aromatic anilide ring can provide a useful hypsochromic shift in image dye hue. In general, however, the light stability of the dyes resulting from such couplers is inferior to that of dyes from couplers with alternative substituents in this position (e.g. chloro). Improvements in light stability can be made through the incorporation of certain stabilizing addenda (e.g. blocked bis-phenols) in the coupler dispersion, but, in general, the alkoxy-substituted couplers remain disadvantaged in image dye stability.

U.S. Pat. Nos. 4,910,126; 5,215,877; 5,219,716; 5,270, 156; 5,324,625; 5,336,592; 5,340,703; 5,346,809; 5,376, 508; 5,380,639 and 5,382,506 each describe a photographic material comprising a silver emulsion layer containing a substituted acetanilide coupler, disclosing advantages in, for example, raw stock stability and stability to pH fluctuations; lowered fog; color reproducibility and dispersion stability. No evidence is provided in any of these specifications for any improvement in light stability of the yellow dye images by the use of these couplers, nor of any superiority in properties by the selection of a 2-alkoxy acetanilide wherein the alkyl group attached to the oxygen atom is a secondary or tertiary alkyl group.

PROBLEM TO BE SOLVED BY THE INVENTION

It is well known in the art of coupler chemistry that when a functionality is incorporated into a molecule to achieve one of the aforementioned desirable properties (such as good dye light stability), quite often one or more of the other desirable properties of the photographically formed dye (such as its hue) is affected adversely. It is very difficult to obtain a coupler which manifests all or even most of the aforementioned desirable properties. Yellow dye-forming couplers of the general acetanilide type are well known in the art of photography; however there is still a need for couplers which give rise to dyes which have very good stability against the deleterious effects of exposure to light but which at the same time retain all or most of the aforementioned desirable properties.

SUMMARY OF THE INVENTION

It has now been found that a particularly beneficial combination of properties and in particular unexpected and substantial improvements in image dye stability towards fading by light can be obtained, whilst retaining all or most of the other desirable properties which have already been mentioned, by increasing the steric bulk of the alkyl substituent in the 2-position of the aromatic anilide ring of acetanilide based couplers. Furthermore, couplers of the latter type are more amenable to stabilization by the aforementioned stabilizing addenda.

According to the present invention therefore there is provided a coupler of formula (Ia)

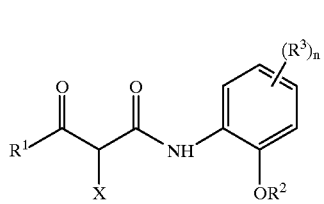

(Ia)

wherein $R^1$ is selected from an alkyl group, an aryl group, a 5–10 membered heterocyclic group containing one or more O, N or S atoms, each of which groups is unsubstituted or substituted, or a substituted amino group;

$R^2$ is an unsubstituted alkyl group having a secondary or tertiary carbon atom attached to the oxygen atom;

X is hydrogen or a coupling-off group; and $R^3$ is a substituent and n is 0 to 4; or wherein $R^2$, as defined above, and an $R^3$ substituent may together with the O atom form a 5–10 membered heterocyclic group which may contain one or more further heteroatoms selected from O, N and S, said group being unsubstituted or substituted; and wherein at least one of $R^1$, $R^2$ and $R^3$ separately or in combination constitutes a ballast group;

provided that (a) when $R^2$ is i-propyl, $R^3$ may not in the 5-position be an unsubstituted alkylamido or unsubstituted alkylsulfonamido group, or the group —CONH $(CH_2)_3CONHC_6H_4C_{12}H_{25}(p)$, —NHCO$(CH_2)_3$ COOC$_6H_4C_{12}H_{25}$-p or —SO$_2$NHC$_{12}H_{25}$(n);

(b) when $R^2$ is cyclohexyl, $R^3$ may not in the 5-position be an unsubstituted alkylamido or unsubstituted alkylsulfonamido group, or the group —CONHCH($C_2H_5$) $CH_2SO_2C_6H_3[2-OCH_3,5-C_8H_{17}(t)]$; or (c) when $R^2$ is t-butyl, $R^3$ may not in the 5-position be the —NHSO$_2C_6H_4OC_{12}H_{25}$(p).

In a particular embodiment there is provided a compound of formula (Ib)

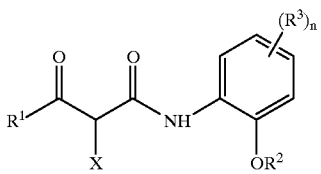

(Ib)

wherein, subject to the above provisos,

R³ is an unsubstituted or substituted alkyl, COOR, NHCOR, NHSO₂R, SO₂NHR or OSO₂R group, where R is an optionally substituted alkyl, aryl or heterocyclic group.

In a more preferred embodiment R³ is an unsubstituted or substituted COOR group, generally at the 3-, 4- or 5-position, most preferably at the 5-position.

The present invention also includes a photographic element containing a compound of formula (Ia) as an image dye-forming coupler, in association with a light sensitive silver halide emulsion layer.

In yet another aspect the present invention provides a multi-color photographic material comprising a support bearing yellow, magenta and cyan dye image-forming units, comprising at least one blue-, green- or red-sensitive silver halide emulsion layer having associated therewith at least one yellow, magenta or cyan dye-forming coupler respectively, wherein at least one dye-forming coupler is a coupler of formula (Ia) in accordance with the present invention.

In another aspect the present invention provides the use of a coupler of formula (I) capable of forming a dye by reaction with oxidised color developing agent in a photographic material comprising a support bearing a light-sensitive silver halide emulsion layer in association therewith to provide an image of enhanced light stability combined with acceptable dye hue, wherein the coupler has the formula (I)

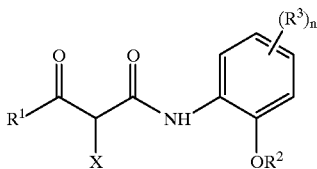

(I)

wherein

R¹ is selected from an alkyl group, an aryl group, a 5–10 membered heterocyclic group containing one or more O, N or S atoms, each of which groups is unsubstituted or substituted, or a substituted amino group;

R² is an unsubstituted alkyl group having a secondary or tertiary carbon atom attached to the oxygen atom;

X is hydrogen or a coupling-off group; and

R³ is a substituent and n is 0 to 4; or wherein R², as defined above, and an R³ substituent may together with the O atom form a 5–10 membered heterocyclic group which may contain one or more further heteroatoms selected from O, N and S, said group being unsubstituted or substituted; and wherein at least one of R¹, R² and R³ separately or in combination constitutes a ballast group.

In further embodiments of the invention there are provided the use of a coupler of formula (I) in combination with an image stabiliser, in particular a phenolic stabiliser, and a photographic element and a multicolor photographic material containing such a combination.

DETAILED DESCRIPTION OF THE INVENTION

The invention will now be described in greater detail. While the invention will be described primarily with reference to a typical color paper format, it will be readily apparent that the invention will apply as well to additional photographic element formats. Thus the advantages of the invention are particularly useful for direct viewing of color print elements designed for such viewing including print elements on reflective supports and motion picture print film and other projection or display films on transparent or diffuse supports.

In couplers of formula (I) or (Ia) typically R¹ may be selected from primary, secondary or tertiary alkyl, phenyl, thiophenyl, pyrrolyl, indolyl, 2,3-dihydro-indolyl, all of which may be unsubstituted or substituted, or substituted amino. Preferably R¹ is a tertiary alkyl group and especially t-butyl.

Preferably R² is a unsubstituted secondary alkyl group having 3 to 20 carbon atoms, the groups attached to the secondary carbon atom being either the same or different. If R¹ and/or R³ contains a ballast group R² will generally have from 3 to 12 carbon atoms, more preferably 3 to 6 carbon atoms. In a particular embodiment R² is an isopropyl group.

R³ may be selected from coupler solubilising, ballasting groups and dye hue-modifying groups. In particular subject to the foregoing proviso for compounds of formula (Ia), R³ may be selected from halogen, alkyl, aryl, heterocyclic, carboxylic acid, alkoxy- or aryloxy-carbonyl, primary or secondary alkyl- or aryl-amido, alkyl- or aryl-sulfonamido, primary, secondary or tertiary amino, alkoxy, aryloxy, acyloxy, alkyl- or aryl-carbamoyl, alkyl- or aryl-sulfamoyl, alkyl and aryl-sulfonyl and alkyl- or aryl-sulfonyloxy.

Preferably n is 1 and R³ is located at the 3-, 4- or 5-position, preferably at the 5-position.

The coupling-off group is a group adapted to split off from the coupler as the result of the reaction between the coupler and the oxidation product of an arylamine color developer. It will be appreciated that X may be hydrogen or any coupling-off group known to a person skilled in the art. In some embodiments the coupling-off group may be selected from halogen, acyloxy, sulfonyloxy, aryloxy, heteroaryloxy, arylthio, heteroarylthio, urethane, imido, 2,4-oxazolidinedione, pyridone, pyridazone, phthalimide, succinimide, hydantoin, triazole, triazoledione, thiazoledione, tetrazole, imidazole, pyrazole and benzotriazole.

In particular unless otherwise specified, either of R¹ and R³ (other than halogen) and the coupling-off group may be substituted with one or more of the same or different groups as hereinbefore defined for R³, each of which may be further so substituted. Usually the substituent will have less than 30 carbon atoms and typically less than 20 carbon atoms. It is understood throughout this specification that any reference to a substituent by the identification of a group containing a substitutable hydrogen (e.g. alkyl, amine, aryl, alkoxy, heterocyclic etc.), unless otherwise specifically stated, shall encompass not only the substituent's unsubstituted form, but also its form substituted with any other photographically useful substituent as known in the photographic art.

As defined herein and throughout the specification unless otherwise stated the term 'alkyl group' includes a straight or branched chain alkyl group, which may be saturated or unsaturated, and includes specifically cycloalkyl groups having from 3 to 10 carbon atoms, such as, for example cyclopropyl and adamantyl. With respect to $R^1$ and $R^3$, the alkyl group may have from 1 to 20 carbon atoms, preferably 1 to 12 carbon atoms and in some embodiments may have conveniently 1 to 4 carbon atoms, subject to the condition that at least one of $R^1$, $R^2$ and $R^3$ must contain separately or in combination a ballast group, i.e. a group sufficiently oleophilic to render the molecule non-diffusible in a photographic layer. Typically the sum of the alkyl groups may contain at least 15 carbon atoms.

Although $R^2$ is, by definition, an unsubstituted alkyl group, it will be apparent from the above that branching with alkyl groups at any further position along the carbon chain is within its scope.

Various image stabilisers that improve image preservability may be used in conjunction with the elements of this invention. Such stabilisers can include any described in the art, including epoxides, sulfinates, hydroxylamines, hindered phenols, bis-phenols, electron-rich aromatic compounds and other polymers. Specific stabilisers that can be used include, but are not limited to, those described in Section X D of *Research Disclosure* September 1994, Item 36544 published by Kenneth Mason Publications Ltd., Dudley House, 12 North Street, Emsworth, Hampshire PO10 7DQ, England, the contents of which are incorporated herein by reference.

Conveniently the stabiliser may be a phenolic stabiliser. In particular it has been found that the stabiliser (S1) having the formula below is useful in further improving light stability.

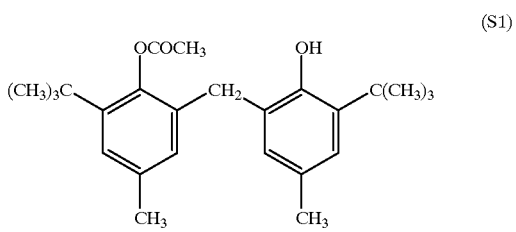

(S1)

When a stabiliser is present it may be combined with the coupler in the ratio by weight of stabilizer:coupler from about 0.1:1 to 2:1, preferably 0.2:1 to 1:1, more preferably 0.3:1 to 0.6:1.

It has been found surprisingly that the introduction of the branched alkyl chain into the acetanilide coupler structure at the 2-position gives rise to an image which is both intrinsically more stable to light and moreover is more susceptible to stabilisation by compounds such as S1. Thus the improvement in light stability by the incorporation of a stabiliser in the photographic material is greater for the couplers of the invention than for the comparison couplers as will be illustrated hereinafter.

The following structures illustrate some specific examples of the couplers of the invention.

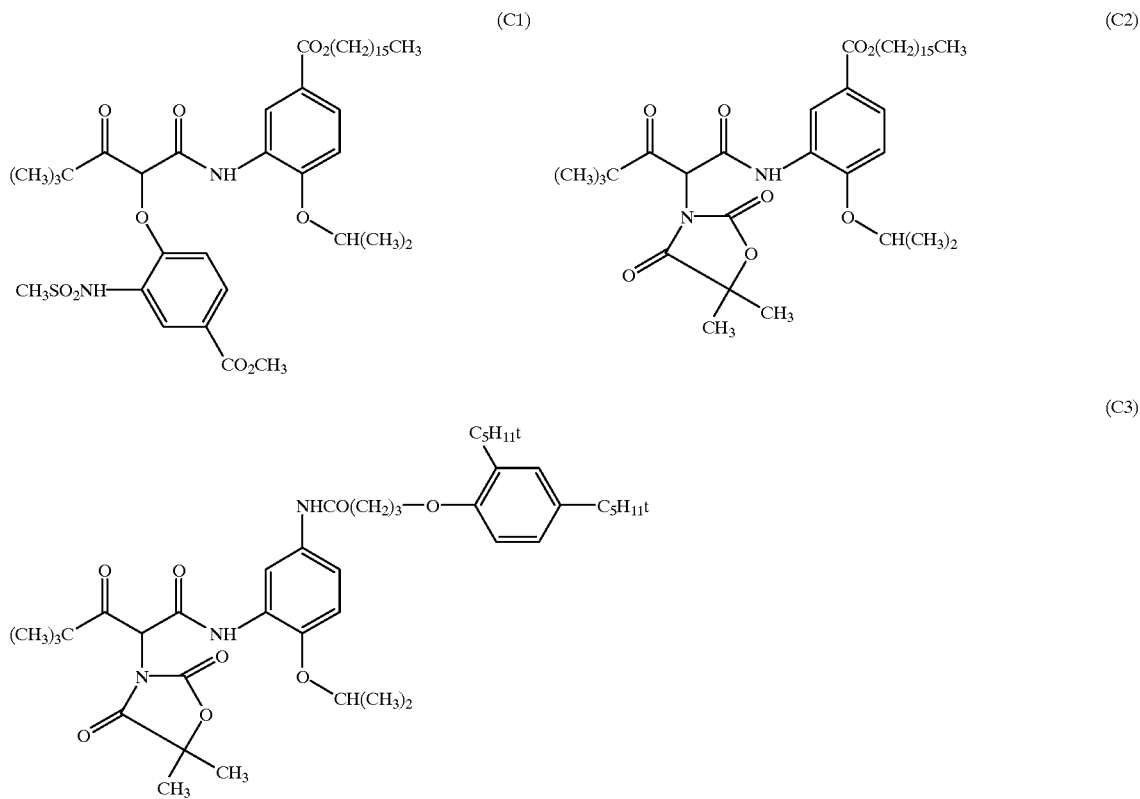

(C4)
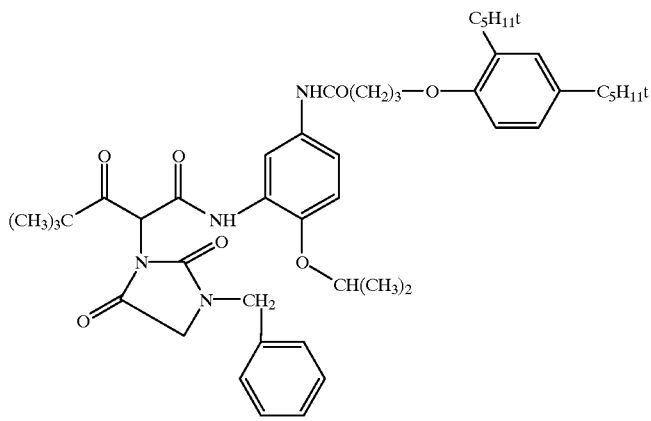
(C5)
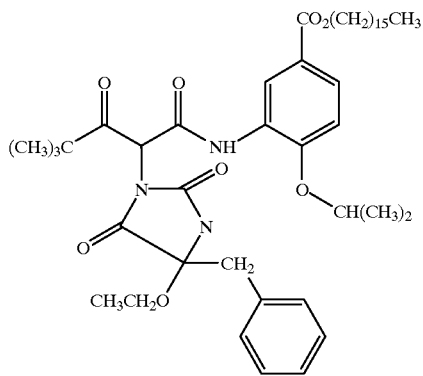
(C6)
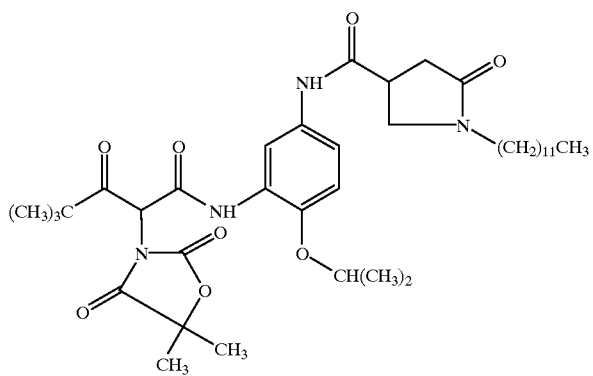
(C7)
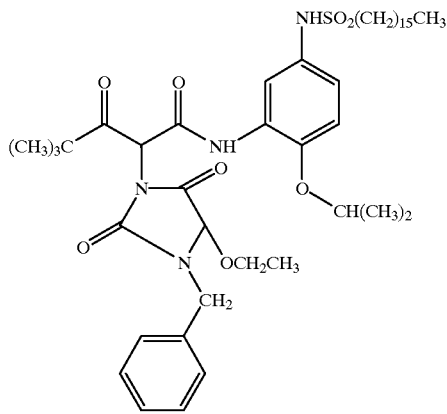

-continued
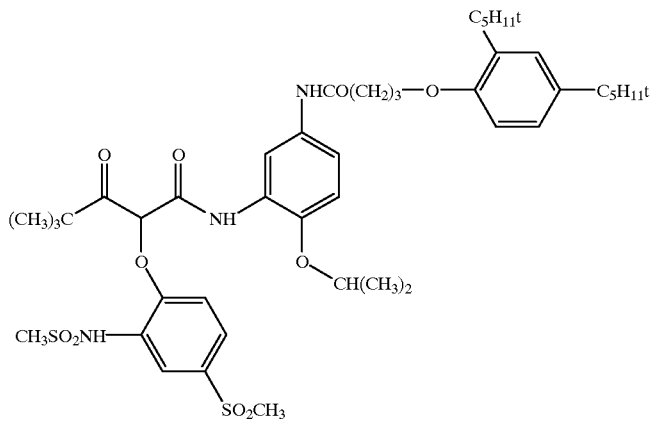
(C8)
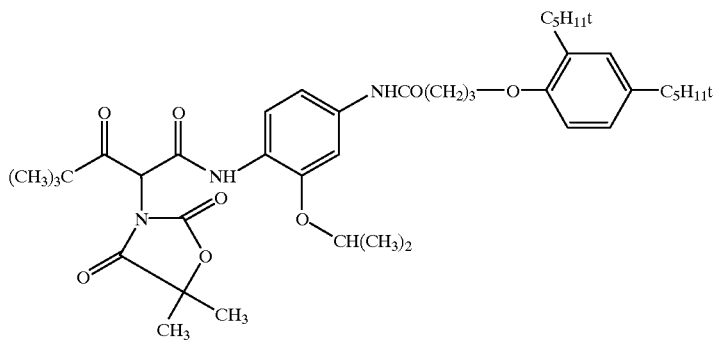
(C9)
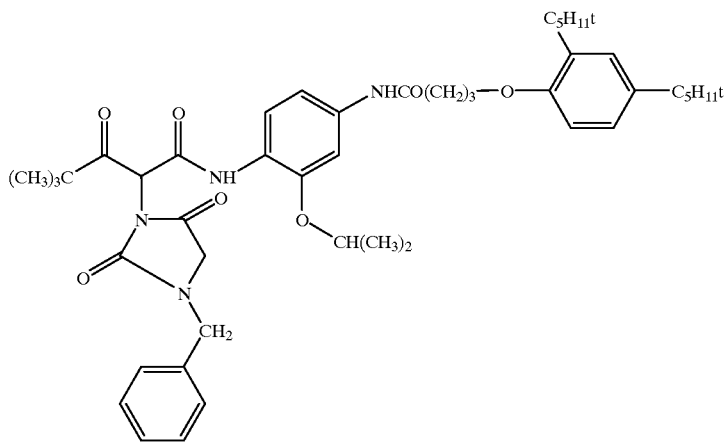
(C10)
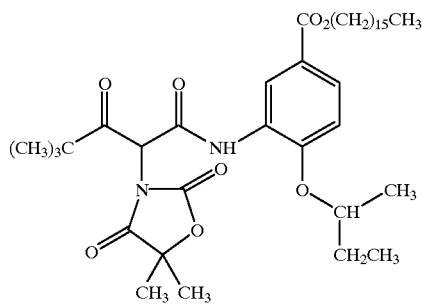
(C11)
(C12)

-continued
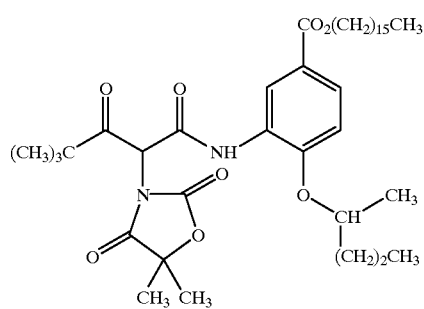
(C13)
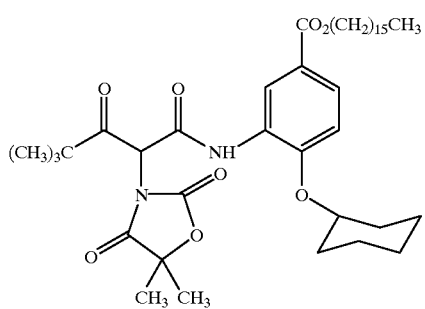
(C14)
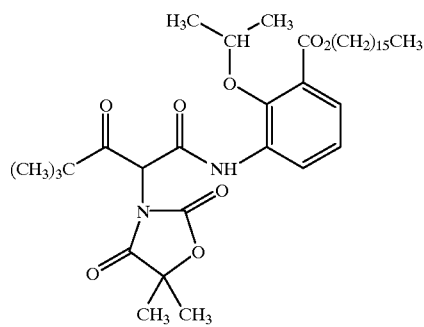
(C15)
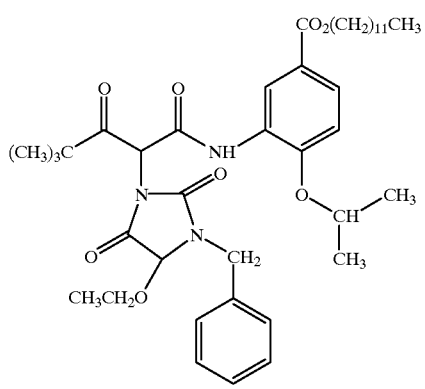
(C16)
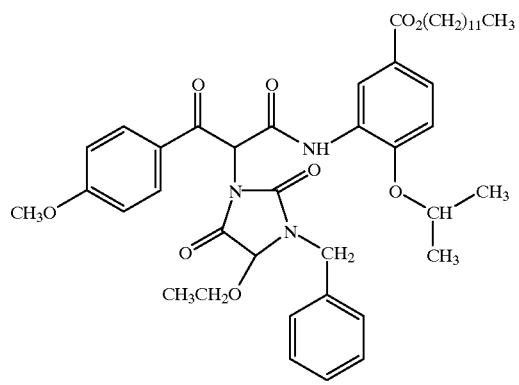
(C17)
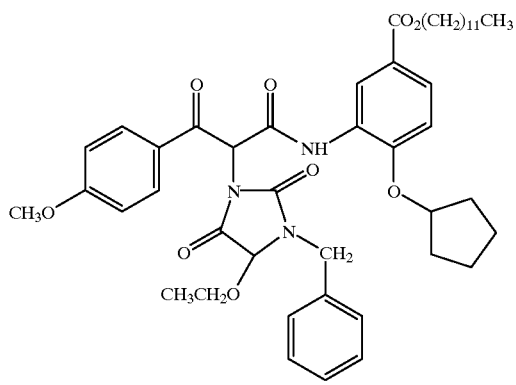
(C18)
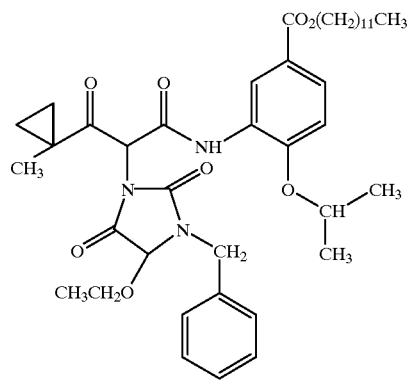
(C19)
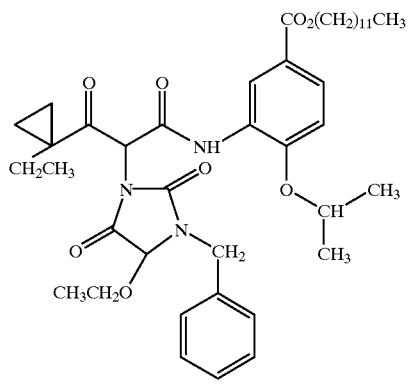
(C20)

-continued
(C21) 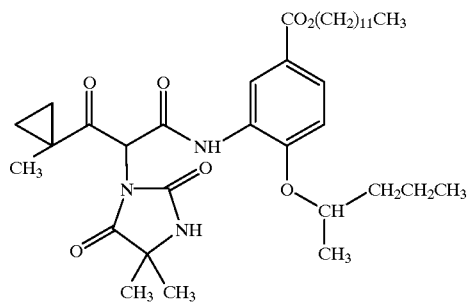
(C22) 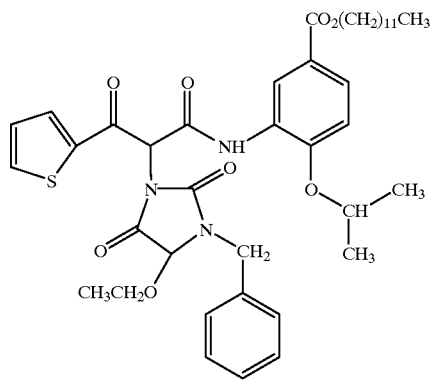
(C23) 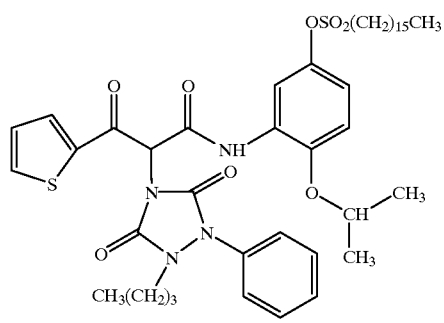
(C24) 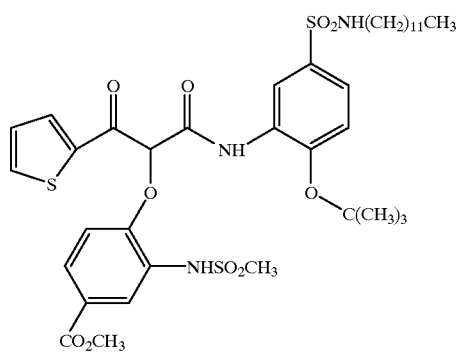
(C25) 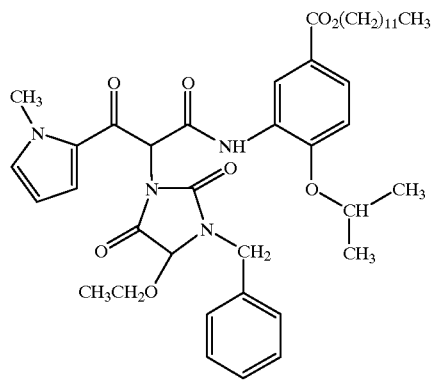
(C26) 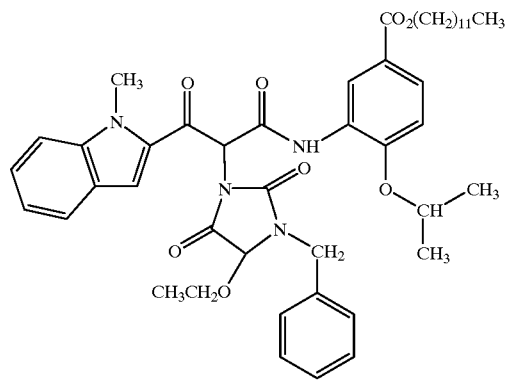
(C27) 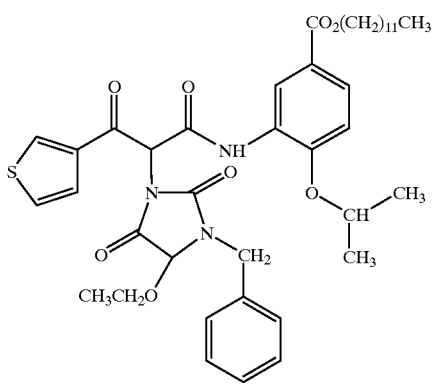
(C28) 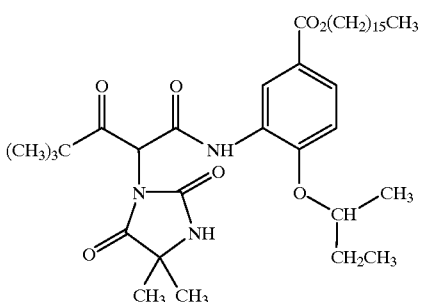

-continued
(C29)
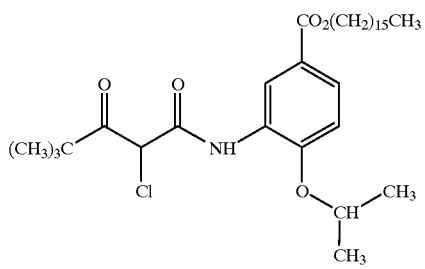
(C30)
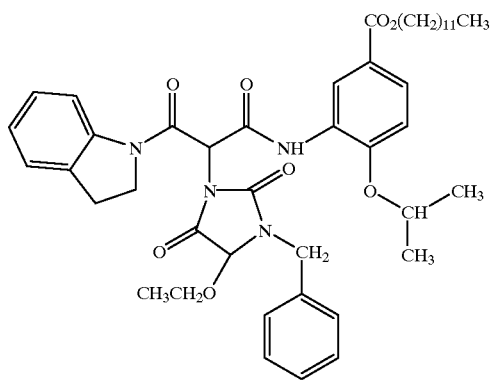
(C31)
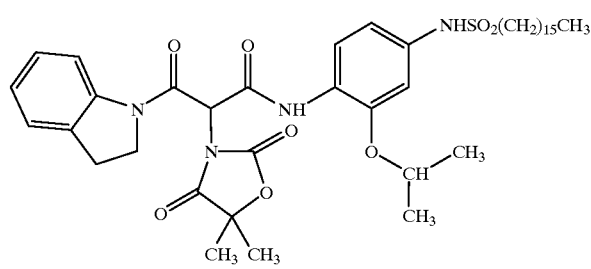
(C32)
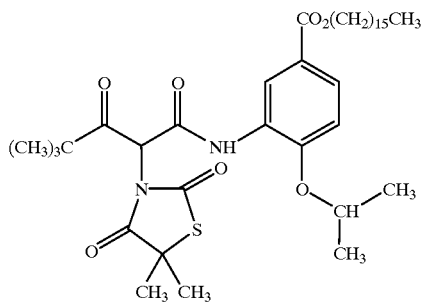
(C33)
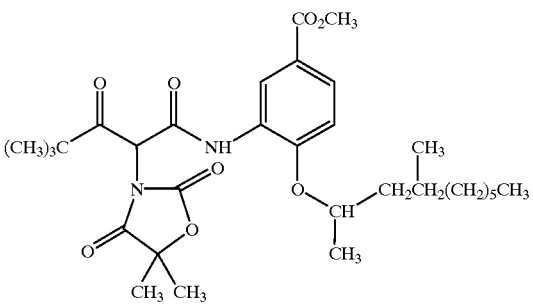
(C34)
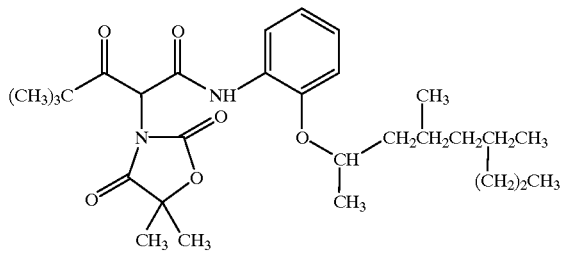
(C35)
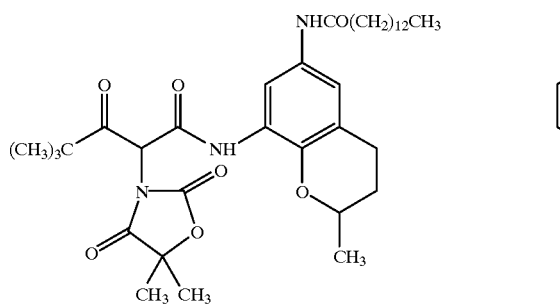
(C36)
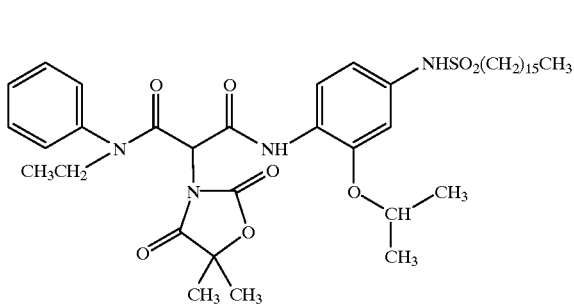

-continued

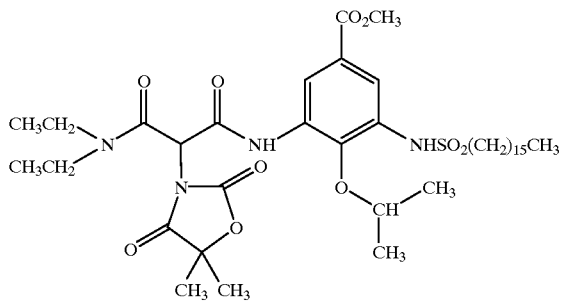
(C37)

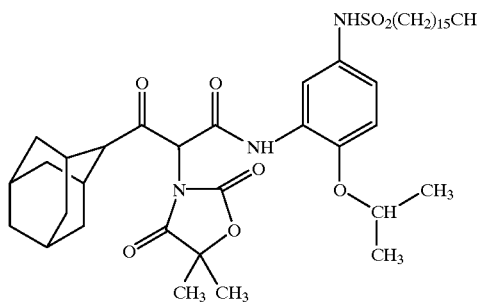
(C38)

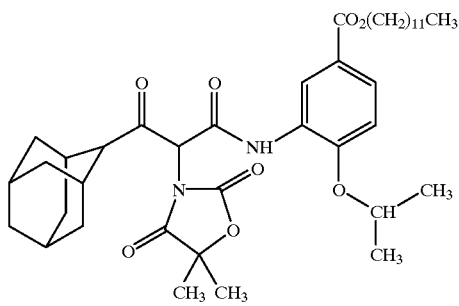
(C39)

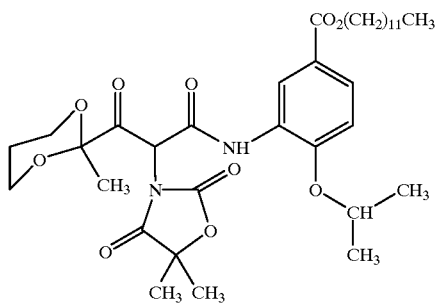
(C40)

Unless otherwise specifically stated, the term substituted or substituent means any group or atom other than hydrogen bonded to the remainder of a molecule. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecylphenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a silver halide emulsion and the emulsion coated as a layer on a support to form part of a photographic element. Alternatively, unless provided otherwise, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

The photographic element may be a single color element or a multicolor element. Multicolor elements contain image dye-forming units sensitive to each of the three primary regions of the visible range of the electromagnetic spectrum. Each unit may comprise a single emulsion layer or a plurality of emulsion layers sensitive to a given region of the spectrum. The layers of the element, including the layers of the image dye-forming units, may be arranged in various orders as known in the art. In an alternative format, the emulsions sensitive to each of the three primary regions of the spectrum may be disposed as a single segmented layer.

A typical multicolor photographic element comprises a support bearing a cyan image dye-forming unit comprising at least one red-sensitive silver halide emulsion layer having associated therewith at least one cyan dye-forming coupler, a magenta image dye-forming unit comprising at least one green-sensitive silver halide emulsion layer having associated therewith at least one magenta dye-forming coupler, and a yellow image dye-forming unit comprising at least one blue-sensitive silver halide emulsion layer having associated therewith at least one yellow dye-forming coupler. The element may contain additional layers, such as, for example, filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications Ltd., Dudley Annex, 12a North Street, Emsworth, Hampshire, PO10 7DQ, England, the contents of which are incorporated herein by reference. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure* Item 36544, September 1994, available as described above, which will be identified hereafter by the term "Research Disclosure". The contents of the Research Disclosure, including the patents and publications referenced therein, are incorporated herein by reference, and the Sections hereafter referred to are Sections of the Research Disclosure.

The silver halide emulsions employed in the elements of this invention can be either negative-working or positive-working. Suitable emulsions and their preparation as well as methods of chemical and spectral sensitisation are described in Sections I through IV. Various additives such as UV dyes, brighteners, antifoggants, stabilisers, light absorbing and scattering materials and physical property modifying addenda such as hardeners, coating aids, plasticizers, lubricants and matting agents are described, for example, in section II and VI through IX. Color materials are described in Sections X through XVIII. Scan facilitating is described in XIV. Supports, exposure, development systems, and processing methods and agents are described in Sections XV to XX. Certain desirable photographic elements and processing steps are described in Research Disclosure, Item 37038, February 1995.

With negative working silver halide a negative image can be formed. Optionally a positive (or reversal) image can be formed.

The color developing agent may be selected from p-phenylene diamines; typically the agent may be selected from:

4-amino-N,N-diethylaniline hydrochloride,
  4-amino-3-methyl-N,N-diethylaniline hydrochloride,
  4-amino-3-methyl-N-ethyl-N-β-(methane-sulphonamidoethyl)aniline sesquisulphate hydrate, 4-amino-3-methyl-N-ethyl-N-β-hydroxyethylaniline sulphate, 4-amino-3-β-(methanesulphonamido)ethyl-N,N-diethylaniline hydrochloride and 4-amino-N-ethyl-N-(2-methoxyethyl)-m-toluidine di-p-toluene sulfonate.

The yellow coupler in accordance with the invention may be used in combination with other classes of image couplers such as 3-acylamino and 3-anilino-5 pyrazoles and heterocyclic couplers (e.g.pyrazoloazoles) such as, for example, those described in EP 285,274, U.S. Pat. No. 4,540,654 and EP 119,860; and other 5-pyrazolone couplers containing different ballasts or coupling-off groups such as, for example, those described in U.S. Pat. Nos. 4,301,235; 4,853,319 and 4,351,897. Yellow or cyan colored couplers (e.g. to adjust levels of interlayer correction) and/or masking couplers such as, for example, those described in EP 213,490, Japanese Published Application 58-172,647, U.S. Pat. No. 2,983,608, German Application DE 2,706,117C, U.K. Patent 1,530,272, Japanese Application A-113935, U.S. Pat. No. 4,070,191 and German Application No. DE 2,643,965 may also be used. Said masking couplers may be shifted or blocked.

Photographically useful coupling-off groups ('PUGS') are well known in the art. Such groups can determine the equivalency of the coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, development acceleration or inhibition, bleach acceleration or inhibition, electron transfer facilitation, color correction and the like.

Representative classes of coupling-off groups include halogen, alkoxy, aryloxy, heteryloxy, sulfonyloxy, acyloxy, acyl, heterocyclyl, sulphonamido, mercaptotetrazole, mercaptopropionic acid, phosphonyloxy, arylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in U.K. Patents and published application Nos. 1,466,728, 1,531,927, 1,533,039, 2,006,755A and 2,017,704A, the disclosures of which are incorporated herein by reference.

The coupler of the present invention may be used in association with materials that accelerate or otherwise modify the processing steps e.g. of bleaching or fixing to improve the quality of the image. Bleach accelerators described in EP 193,389; EP 301,477; U.S. Pat. No. 4,163,669; U.S. Pat. No. 4,865,956; and U.S. Pat. No. 4,923,784 are particularly useful. Also contemplated is the use of the couplers in association with nucleating agents, development accelerators or their precursors (UK Patent 2,097,140; U.K. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulphonamidophenols; and non color-forming couplers.

The yellow coupler may be used in combination with filter dye layers comprising colloidal silver sol or yellow and/or magenta filter dyes, either as oil-in-water dispersions, latex dispersions or as solid particle dispersions. Additionally they may be used with 'smearing' couplers (e.g. as described in U.S. Pat. No. 4,366,237; EP 96,570; U.S. Pat. No. 4,420,556 and U.S. Pat. No. 4,543,323). Also the couplers may in some embodiments be blocked or coated in protected form as described, for example, in Japanese Application 61/258,249 or U.S. Pat. No. 5,019,492.

The yellow coupler may further be used in combination with image-modifying compounds such as Developer Inhibitor-Releasing compounds (DIR's). DIR's useful in conjunction with said couplers are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612 and 401,613.

Such compounds are also disclosed in "Developer-Inhibitor-Releasing (DIR) Couplers for Color Photography," C. R. Barr, J. R. Thirtle and P. W. Vittum in Photographic Science and Engineering, Vol. 13, p. 174 (1969), incorporated herein by reference.

Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptothiatriazoles, mercaptooxadiazoles, mercaptodiazoles, mercaptooxathiazoles, tellurotetrazoles or benzisodiazoles The invention will now be described with reference to the following examples which in no way are to be construed as limiting the scope of the invention.

EXAMPLE 1

Synthesis

The following preparation of the coupler C2 is illustrative for all the couplers of this invention. All the compounds prepared had infra-red, mass and NMR spectra which were in accord with sufficiently pure samples of the desired products.

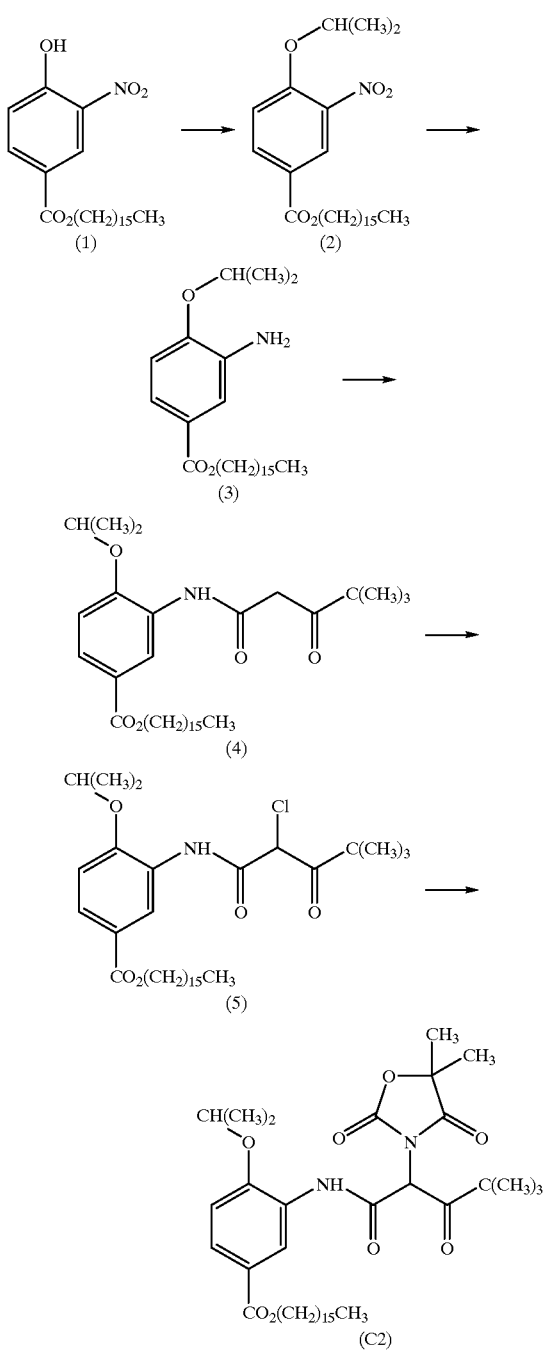

Compound (1) can be prepared from readily available 4-hydroxy-3-nitrobenzoic acid by standard esterification procedures.

Compound (2) The ester (1) (39.3 g, 0.097 mol), anhydrous potassium carbonate (50 g, 0.362 mol) and isopropyl bromide (13.53 g, 0.11 mol) were added to a three-necked flask fitted with a magnetic stirrer. Dimethylformamide (300 ml) was added and the mixture stirred and heated to 110° C. (oil bath temperature) for 3 h. Further portions of isopropyl bromide (total of 8.0 g) were added to the reaction mixture over the course of the following 4 h. The mixture was allowed to cool and poured into water (3 l) with stirring. The pale yellow precipitate was filtered, washed with water and dried under vacuum at 40° C. Yield: 37.7 g (87%).

Compound (3) The nitro compound (2) (50 g, 0.11 mol) was dissolved in tetrahydrofuran (500 ml) and 5% palladium on carbon catalyst (0.3 g) was added. The mixture was hydrogenated at room temperature overnight under 34 atmospheres pressure of hydrogen. The catalyst was filtered off and the solvent removed under reduced pressure. The product was obtained as an oil which gradually solidified. Yield: 40.6 g (89%).

Compound (4) Amine (3) (40.6 g, 0.097 mol) and methyl pivaloylacetate (17.4 g, 0.11 mol) were dissolved in heptane (1 l) and heated to reflux for 2 h in a Soxhlet apparatus containing 4A molecular sieve. A further quantity of methyl pivaloylacetate (2.0 g) was added and the mixture heated for a further 5 h. The reaction was allowed to stand overnight. The product was obtained as white crystals which were filtered, washed with heptane and dried under vacuum. Yield: 48.3 g (91%).

Compound (5) Coupler (4) (40.0 g, 0.073 mol) was dissolved in dichloromethane (600 ml). Sulfuryl chloride (9.9 g, 0.0733 mol) in dichloromethane (50 ml) was added dropwise to the coupler solution with stirring. The mixture was allowed to stand overnight. The solvent was removed under reduced pressure and the residual oil solidified to a white powder. Yield: 42.5 g (quantitative).

Coupler (C2) Coupler (5) (42.5 g, 0.0732 mol), dimethyl oxazolidinedione (9.7 g, 0.075 mol) and triethylamine (7.6 g, 0.075 mol) were dissolved in acetonitrile (750 ml) and heated to reflux. After 1 h, further dimethyl oxazolidinedione (2.0 g) was added. The mixture was heated for a further 3 h. The volume of the solution was reduced (to around 150 ml) under reduced pressure and the mixture poured onto ice/-hydrochloric acid (2 l ice/10 ml conc. hydrochloric acid). The product was filtered, dried under vacuum and recrystallized twice from heptane. The coupler (C2) was obtained as pure white crystals. Yield: 38.0 g (77%).

| $C_{38}H_{60}N_2O_8$ | Requires: | C; 67.82 | H; 8.99 | N; 4.16 |
|---|---|---|---|---|
| | Found: | C; 67.42 | H; 8.82 | N; 4.08 |

The couplers of the invention were compared with comparison couplers.

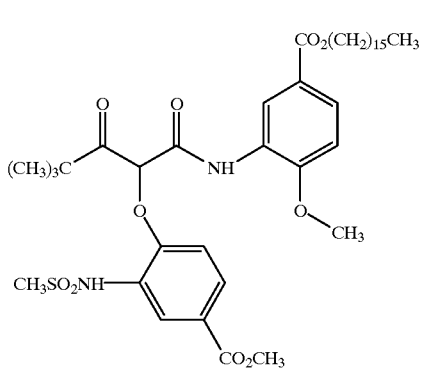

(A1)

(A2)
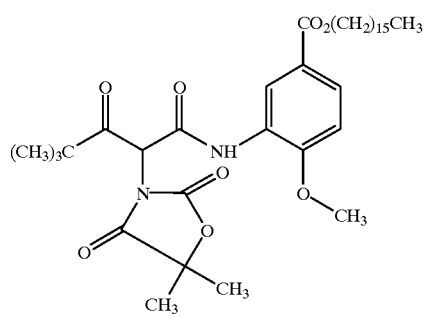
(A3)
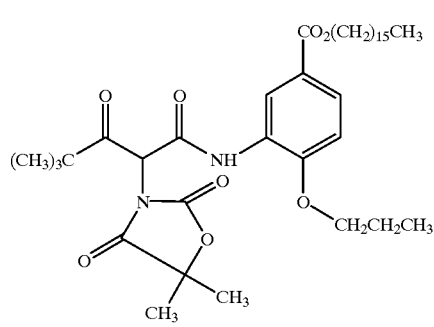
(A4)
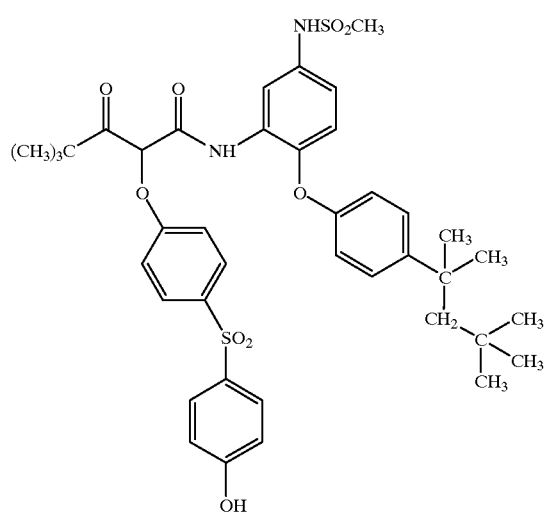
(A5)
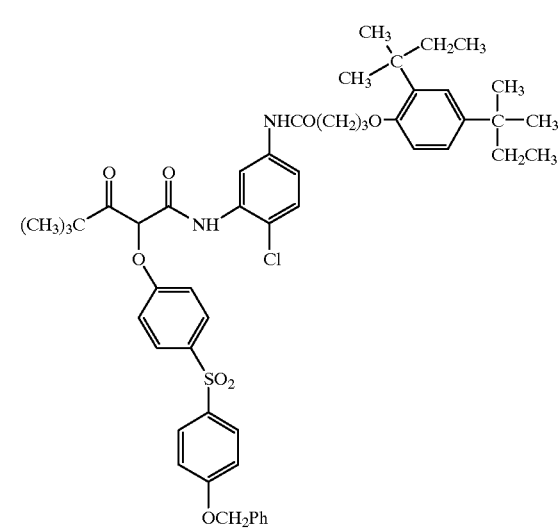
(A6)
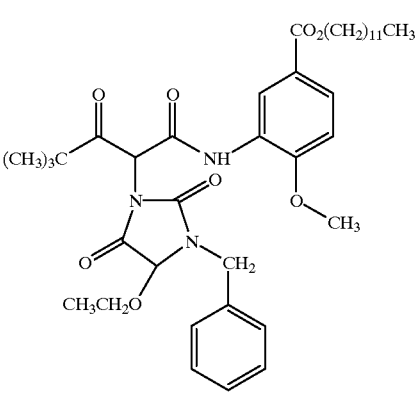
(A7)
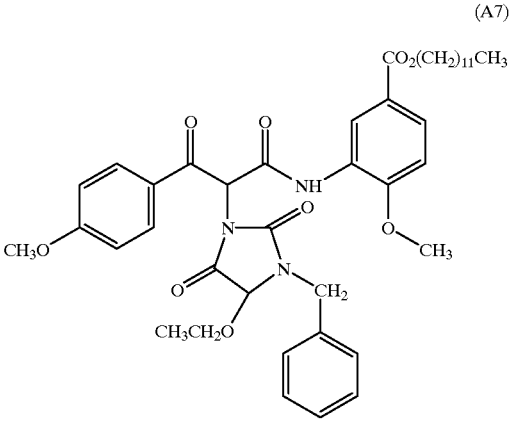

EXAMPLE 2

Example coupler C1 was dispersed in gelatin according to the following procedure: Coupler C1 (6.60 g, 8.38 mmol) was mixed with the stabilizer S1 (1.58 g) and dissolved in a mixture of n-butyl phthalate (2.18 g), 2-(2-butoxyethoxy) ethyl acetate (1.85 g) and ethyl acetate (2.0 g). The hot oil phase solution was mixed with aqueous gelatin (40 g, 10.9%) which also contained 0.25% of di-isopropylnaphthalene sulphonic acid (sodium salt) and 1.6% Pluronic™ L44 surfactant (ICI). The gelatin was held at 40° C. prior to mixing and the mixture was dispersed immediately, using ultrasonic agitation (Dawe Instruments "SONIPROBE"), for 2 min.

A further dispersion was similarly prepared using the same molar quantity (6.37 g) of the comparison coupler A1 in place of C1. The amounts of the other components in the oil phase were reduced accordingly to maintain the original proportionality by weight, thus:

| Coupler: | 1.0 |
|---|---|
| Stabilizer S1: | 0.24 |
| Dibutyl phthalate: | 0.33 |

Comparison couplers A4 and A5 were dispersed in the same fashion.

Each of the above coupler dispersions was diluted with further aqueous gelatin and mixed with a blue-sensitive cubic silver chloride photographic emulsion (average edge length: 0.76 mm) for coating on a resin-coated paper support, pre-coated with an unhardened gel pad. The mixing of the already molten components was carried out immediately prior to coating. A protective gel layer, to which was added an appropriate quantity of bis-(vinylsulfonylmethyl) ether hardener, was coated over the photosensitive layer. The full coating structure is shown below (stabilizer and/or solvent coverages in the photosensitive layer are defined by the quoted coupler coverage, depending on dispersion type).

Sample strips of the coatings were exposed through a step tablet (density range 0–3, 0.15 inc.) and developed with a redox-amplified color developer solution (32 s at 35° C.). A stop-bath was included after the development stage, and the image was bleached with standard Kodak Ektacolor RA™ bleach-fix solution before washing and drying. The formulae for the developer and stop-bath are given below.

| Resin Coated Paper | | |
|---|---|---|
| Gel | 1.615 g/m$^2$ | GEL SUPERCOAT |
| Hardener* | 0.093 g/m$^2$ | |
| Coupler | 0.750 mM/m$^2$ | PHOTOSENSITIVE LAYER |
| Ag | 0.035 g/m$^2$ | |
| Gel | 1.615 g/m$^2$ | |
| Gel | 3.0 g/m$^2$ | GEL PAD |

*Hardener = bis(vinylsulfonylmethyl) ether

| Developer Composition: | |
|---|---|
| AntiCal-4$^+$ | 5.0 g/l |
| AntiCal-8$^{++}$ | 0.81 g/l |
| K$_2$HPO$_4$.3H$_2$O | 40.0 g/l |
| Potassium bromide | 0.0015 g/l |
| Potassium chloride | 0.4 g/l |

| -continued | |
|---|---|
| Developer Composition: | |
| Hydroxylamine sulphate | 1.2 g/l |
| Catechol disulfonate | 0.3 g/l |
| Developer* | 5.5 g/l |
| Tween ™-80** (Atlas Chemicals) | 0.3 g/l |
| Dodecylamine | 0.1 g/l |
| Hydrogen peroxide (H$_2$O$_2$)-30 vol | 2 ml/l |
| (pH adjusted to 11.5 by addition of KOH solution) | |

$^+$AntiCal-4: 40% aqueous solution of pentasodium salt of amino-tris (methylphosphonic acid)
$^{++}$AntiCal-8: 40% aqueous solution of pentasodium salt of diethylenetri-aminepentaacetic acid
*Developer: 4-N-ethyl-N-(2-methanesulphonamido-ethyl)-o-toluidine sesquisulphate
**Tween ™-80: Polyoxyethylenesorbitan mono-oleate

| Stop-bath Composition: with pH adjusted to 5.2 | |
|---|---|
| Sodium metabisulfite | 50 g/l |
| Ammonium thiousulfate | 28 g/l |

Sensitometric curves were generated for each coating and the spectral absorption characteristics of the image dyes were also measured. The image dye light stability was assessed using standard simulated daylight fading equipment incorporating a Xenon arc source, delivering an exposure intensity of 50 Klux at the sample plane. For this, sample strips were mounted in the fader under a UV-absorbing filter, comprising Tinuvin™-328 (Ciba-Geigy), dispersed in gelatin and coated on a transparent polyester sheet at a coverage of 1.0 g/m$^2$. At the end of the test, the sensitometric curves were re-read and compared with the initial curves. Status "A" blue density losses from an initial value of 1.0 were recorded.

The results are reproduced in TABLE 1, which shows the density loss from 1.0 for each sample in the stability test, as well as the wavelength of maximum absorption, read from the spectral absorption curves, to represent the dye hue. The results show very clearly that the image dye from the inventive coupler C1 is substantially more stable to light than that from the related (MeO-substituted) comparison coupler A1. Moreover, while the phenoxy-substituted comparison coupler A4 shows good image dye light stability, the hue of the image dye is inferior to that of coupler C1. The same is true of the comparison coupler A5; its image dye light stability is the best of all those examined, but its bathochromically shifted dye hue is typical of dyes from such chloro-substituted couplers. Only coupler C1 combines good image dye hue and light stability.

TABLE 1

| Image Dye Hue and Stability Data | | |
|---|---|---|
| Coated Dispersion | $\lambda_{MAX}$ (nm) | Light* Stability |
| C1/S1 | 439.6 | −0.49 |
| A1/S1 | 437.8 | −0.71 |
| A4/S1 | 444.9 | −0.40 |
| A5/S1 | 445.9 | −0.29 |

*4 wk, 50 Klux Fade, Density loss from 1.0

EXAMPLE 3

Coupler C2 (5.63 g) was dispersed in gelatin according to the procedure outlined in Example 2, and a second dispersion was also made in the same way, but with the stabilizer S1 omitted from the oil phase composition.

Similar pairs of dispersions were prepared using the comparison couplers A2 and A3 instead of C2. The molar concentration of coupler in the various dispersions was maintained at the level described in Example 2 by appropriate adjustments of the weight of coupler used, proportional adjustments being made for other components of the dispersion oil phase, to maintain the same weight ratios.

The above coupler dispersions were coated using exactly the same procedure as described in Example 2, and were similarly processed to provide sample strips for image stability and hue evaluation. The test procedures exactly matched those described in Example 2.

The results are reproduced in TABLE 2, and show very clearly that the image dye from the inventive coupler C2 is substantially more stable to light than those from either of the two comparison couplers A2 and A3. All the image dyes are stabilized by the presence of the stabilizer S1, but the stability advantage shown by the dye from C2 is maintained in this format also. Moreover, comparison of the light stability figures for the unstabilized and stabilized coupler formulations reveals that coupler C2 gives a dye that is more readily stabilized than either of the comparison couplers. The improvement in dye stability produced by the presence of the stabilizer S1 is greater for coupler C2 than for either A2 or A3. Thus the introduction of the branched alkyl chain into the acetanilide coupler structure gives rise to an eventual image dye which is both intrinsically more stable to light, and more susceptible to stabilization by compounds like S1.

TABLE 2

Image Dye Hue and Stability Data

| Coated Dispersion | $\lambda_{MAX}$ (nm) | Light* Stability |
| --- | --- | --- |
| C2 | 438.2 | −0.51 |
| A3 | 438.5 | −0.72 |
| A2 | 437.8 | −0.75 |
| C2/S1 | 437.8 | −0.17 |
| A3/S1 | 437.7 | −0.27 |
| A2/S1 | 437.6 | −0.40 |

*4 wk, 50 Klux Fade, Density loss from 1.0

EXAMPLE 4

Coupler C2 and the comparison coupler A2 were dispersed in gelatin in a similar fashion to that described in Example 2, but in this case dispersion was effected with a Microfluidizer M-100F high pressure mechanical homogenizer (Microfluidics Corp.). Dibutyl lauramide was used as coupler solvent (in place of dibutyl phthalate). Two different oil phase formulations were used, incorporating the following proportions of the major oil phase components:

| | A | B |
| --- | --- | --- |
| Coupler: | 1.0 | 1.0 |
| Stabilizer S1: | 0.18 | 0.46 |
| Solvent (dibutyl lauramide): | 1.33 | 1.04 |

These dispersions were coated in a similar fashion to that described in Example 2, except that a UV-absorbing layer was included above the imaging layer. Different silver and coupler levels were employed. The structure is shown below.

Development of these coatings was achieved using standard Kodak Ektacolor RA™ solutions and process conditions, but in most other respects the evaluation procedure was as described in Example 2. The only difference was that no external UV-absorbing filter was required in the light stability test.

| Resin Coated Paper | | |
| --- | --- | --- |
| Gel | 1.08 g/m$^2$ | GEL SUPERCOAT |
| Hardener* | 0.14 g/m$^2$ | |
| Tinuvin ™-326 | 0.113 g/m$^2$ | UV-ABSORBER LAYER |
| Tinuvin ™-328 | 0.640 g/m$^2$ | |
| Gel | 1.40 g/m$^2$ | |
| Coupler | 0.800 mM/m$^2$ | PHOTOSENSITIVE LAYER |
| Ag | 0.270 g/m$^2$ | |
| Gel | 1.55 g/m$^2$ | |
| Gel | 3.23 g/m$^2$ | GEL PAD |

*Hardener = bis(vinylsulfonylmethyl) ether

The results of the light stability tests, shown in TABLE 3, demonstrate that the improved performance of the coupler of this invention, C2, in relation to the comparison coupler, A2, is maintained in this coating format and processing regime. Increasing the proportion of the stabilizer S1 in the dispersion improves image dye light stability for both couplers, but does not alter the advantage shown by coupler C2.

TABLE 3

Image Dye Light Stability Data

| Coated Dispersion | Light* Stability | |
| --- | --- | --- |
| | A | B |
| C2/S1 | −0.41 | −0.23 |
| A2/S1 | −0.77 | −0.42 |

*3 wk, 50 Klux Fade, Density loss from 1.0

EXAMPLE 5

The comparison coupler A7 and the two couplers C17 and C18 were dispersed according to the procedure outlined in Example 2, except that the Pluronic™-L44 surfactant was replaced in the aqueous phase by additional di-isopropylnaphthalene sulphonic acid (to a total 0.8%). The same molar quantity of coupler was used in all these dispersions, the amounts of the other oil-phase components being adjusted to maintain the same proportionality to the couplers.

Similar dispersions of the couplers A6 and C16 were also prepared in the same fashion.

Coatings of these dispersions were made as described in Example 2, except that the proportion of the silver chloride photographic emulsion was increased to give a silver coverage of 0.28 g/m$^2$. Development of these coatings was achieved using standard Kodak Ektacolor RA™ processing solutions in place of the redox-amplified process described in Example 2.

Light stability measurements were made as described in Example 2 and the results are reproduced in TABLES 4a and 4b. TABLE 4a shows the density loss from 1.0 after a 3 wk. fade for the coating of C16 (i-PrO-substituted) compared with that for the corresponding MeO-substituted equivalent coupler, A6. The light stability advantage conferred by the branched alkoxy substituent is clearly evident.

TABLE 4a

Image Dye Hue and Stability Data

| Coated Dispersion | $\lambda_{max}$ (nm) | Light* Stability |
|---|---|---|
| A6/S1 | 437.9 | −0.20 |
| C16/S1 | 437.8 | −0.14 |

*3 wk, 50 Klux Fade, Density Loss from 1.0

TABLE 4b shows the corresponding data for C17 and C18, both incorporating a branched alkoxy substituent, compared with the equivalent MeO-substituted variant, A7. Once again, it is clear that incorporation of a branched alkoxy substituent substantially improves image dye light stability.

TABLE 4b

Image Dye Hue and Stability Data

| Coated Dispersion | $\lambda_{max}$ (nm) | Light* Stability |
|---|---|---|
| A7/S1 | 440.5 | −0.37 |
| C17/S1 | 440.9 | −0.22 |
| C18/S1 | 441.3 | −0.18 |

*1 wk, 50 Klux Fade, Density Loss from 1.0

EXAMPLE 6

The comparison couplers A2 and A3 were dispersed according to the procedure outlined in Example 5. except that the stabilizer S1 was omitted from the oil phase. Corresponding dispersions of the couplers C2, C11, C12, and C13 were also prepared in the same fashion.

Coatings of these dispersions, made and processed as described in Example 5, were subjected to the light fade experiment described in Example 2 and the results are shown in TABLE 5, which also includes the wavelength of maximum absorption, read from the spectral absorption curves, to represent the dye hue. These results confirm and amplify those seen in Example 3. All the couplers of this invention, C2, C11, C12 and C13 (which incorporate a branched alkoxy substituent in the molecule) show enhanced image dye light stability when compared with the two straight-chain alkoxy analogues, A2 and A3.

TABLE 5

Image Dye Hue and Stability Data

| Coated Dispersion | $\lambda_{max}$ (nm) | Light* Stability |
|---|---|---|
| A2 | 437.7 | −0.65 |
| A3 | 437.7 | −0.54 |
| C2 | 437.6 | −0.38 |
| C11 | 437.6 | −0.37 |
| C12 | 437.4 | −0.37 |
| C13 | 437.5 | −0.47 |

*3 wk, 50 Klux Fade, Density Loss from 1.0

The entire contents of the patent applications, patents and other publications referred to in this specification are incorporated herein by reference.

What is claimed is:

1. A photographic element comprising a silver halide emulsion having associated therewith a dye-forming coupler of formula (Ia)

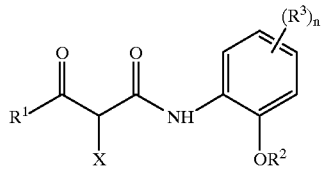

wherein
R$^1$ is selected from an alkyl group, an aryl group, a 5–10 membered heterocyclic group containing one or more O, N or S atoms, each of which groups is unsubstituted or substituted, or a substituted amino group;

R$^2$ is an unsubstituted alkyl group having a secondary or tertiary carbon atom attached to the oxygen atom;

X is hydrogen or a coupling-off group;

R$^3$ is selected from the group consisting of halogen, an unsubstituted alkyl group, an unsubstituted or substituted group selected from aryl, heterocyclic, carboxylic acid, alkoxy-, aryloxy-, and heterocyclyloxy-carbonyl, aryl- and hetcrocyclyl-amido, alkyl-, aryl-, and heterocyclyl-sulfonamido, primary, secondary, and tertiary amino, alkoxy, aryloxy, acyloxy, arylcarbamoyl, alkyl-, aryl-, and heterocyclyl-sulfamoyl, alkyl- and aryl-sulfonyl, and alkyl-, aryl-, and heterocyclyl-sulfonyloxy;

n is 0 to 4;

provided R$^2$ and R$^3$, each as defined above, may together with the O atom form a 5–10 membered heterocyclic group which may contain one or more further heteroatoms selected from O, N and S, said group being unsubstituted or substituted; and, wherein at least one of R$^1$, R$^2$ and R$^3$ separately or in combination constitutes a ballast group; and provided that (a) when R$^2$ is i-propyl, R$^3$ may not in the 5-position be an untsubstituted alkylsulfonamido group or the group —SO$_2$NHC$_{12}$H$_{25}$(n);

(b) when R$^2$ is cyclohexyl, R$^3$ may not in the 5-position be an unsubstituted alkylsulfonamido group;

(c) when R$^2$ is t-butyl, R$^3$ may not in the 5-position be the group —NHSO$_2$C$_6$H$_4$OC$_{12}$H$_{25}$(p).

2. The element according to claim 1 wherein R$^2$ is a unsubstituted secondary alkyl group having 3 to 20 carbon atoms.

3. The element according to claim 2 wherein R$^2$ is an isopropyl group.

4. The element according to claim 1 wherein R$^1$ is a tertiary alkyl group.

5. The element according to claim 4 wherein R$^1$ is a t-butyl group.

6. The element according to claim 1 wherein n is 1.

7. The element according to claim 1 wherein R$^3$ is an unsubstituted or substituted COOR group.

8. The element according to claim 1 wherein the coupling-off group is selected from halogen, aryloxy, hydantoin, triazoledione, dialkyl oxazolidinedione and thiazoledione.

9. An element according to claim 8 which also comprises an image dye stabilizer associated with said coupler.

10. An element according to claim 9 in which the stabilizer is a phenolic compound.

11. An element according to claim 10 wherein the stabilizer is 2-t-butyl-6-[3-t-butyl-2-hydroxy-5-methylbenzyl]-4-methylphenyl acetate.

12. An element according to claim 9 wherein the ratio by weight of stabilizer:coupler is in the range from about 0.1:1 to 2:1.

13. An element according to claim 12 wherein the ratio by weight of stabilizer:coupler is in the range from 0.2:1 to 1:1.

14. An element according to claim 1 which is a color print element designed for direct viewing.

15. An element according to claim 14 which includes a reflective support.

16. An element according to claim 14 which includes a transparent or diffuse support.

17. A multi-color photographic material comprising a support bearing yellow, magenta and cyan dye image-forming units, comprising at least one blue-, green- or red-sensitive silver halide emulsion layer having associated therewith at least one yellow, magenta or cyan dye-forming coupler respectively, wherein at least one dye-forming coupler is a coupler according to claim 1.

18. The element of claim 1 wherein $R^3$ is an unsubstituted alkyl group or an unsubstituted or substituted COOR, $NHSO_2R$, $SO_2NHR$, or $OSO_2R$ group, where R is an optionally substituted alkyl, aryl or heterocyclic group.

19. The element according to claim 7 wherein the COOR group is in the 3-, 4-, or 5-position of the phenyl ring.

20. The element according to claim 19 wherein the COOR group is in the 5-position.

21. The element according to claim 7 wherein $R^3$ is an unsubstituted COOR group.

22. The element according to claim 1 wherein the coupler is selected from the group consisting of:

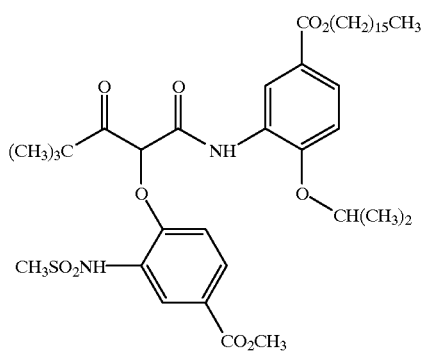
(C1)

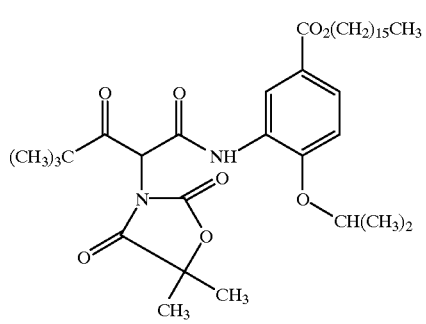
(C2)

-continued

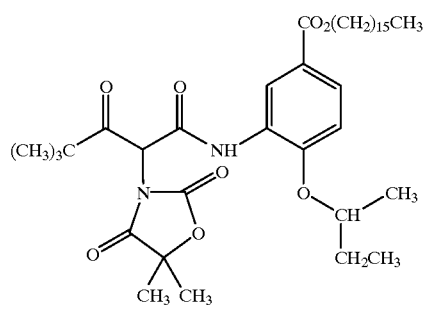
(C11)

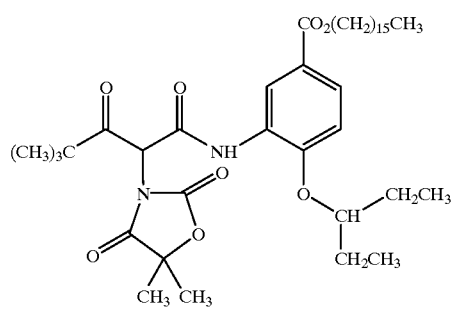
(C12)

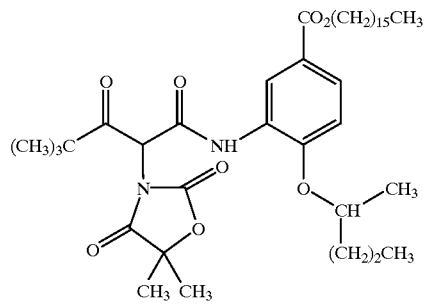
(C13)

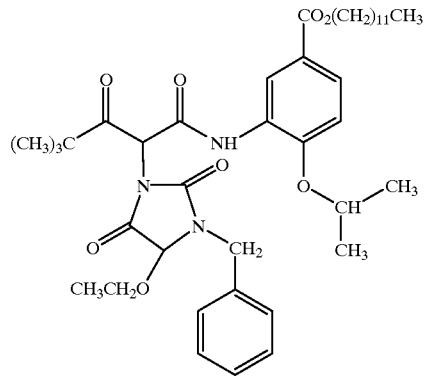
(C16)

-continued
(C17)
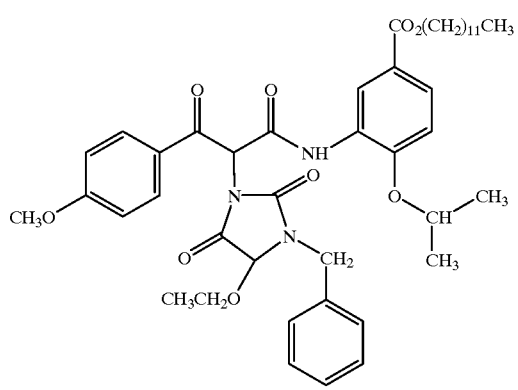
and
(C18)
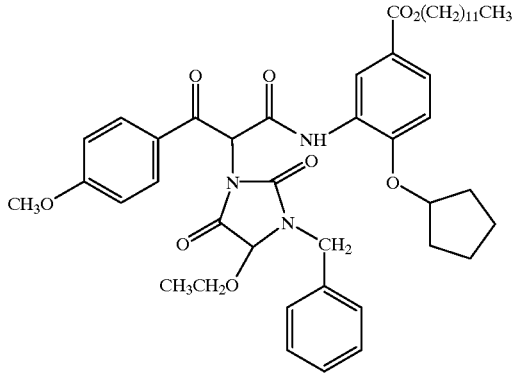
23. The element according to claim 1 wherein the coupler is hexadecyl-3-[2-(2,2-di-methylpropionyl)-2-(5,5-dimethyl-2,4-dioxooxalidin-2-yl)acetamido]-4-isopropyl-oxy-benzoate of structure C2.
* * * * *